(12) United States Patent
Kita et al.

(10) Patent No.: US 10,106,488 B2
(45) Date of Patent: Oct. 23, 2018

(54) HYDROGENATION REACTION METHOD

(71) Applicant: NIPPON SHOKUBAI CO., LTD., Osaka (JP)

(72) Inventors: Yuichi Kita, Hyogo (JP); Yoshiaki Hirano, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/111,263

(22) PCT Filed: Jan. 27, 2015

(86) PCT No.: PCT/JP2015/052161
§ 371 (c)(1),
(2) Date: Jul. 13, 2016

(87) PCT Pub. No.: WO2015/115410
PCT Pub. Date: Aug. 6, 2015

(65) Prior Publication Data
US 2016/0326093 A1 Nov. 10, 2016

(30) Foreign Application Priority Data

Jan. 28, 2014 (JP) ................................ 2014-012925

(51) Int. Cl.
*C07C 209/36* (2006.01)
*C01B 3/08* (2006.01)
(Continued)

(52) U.S. Cl.
CPC ............ *C07C 209/36* (2013.01); *B01J 21/18* (2013.01); *B01J 23/44* (2013.01); *B01J 23/462* (2013.01);
(Continued)

(58) Field of Classification Search
None
See application file for complete search history.

(56) References Cited

U.S. PATENT DOCUMENTS 4,547,356 A * 10/1985 Papineau ............... C01B 3/045
123/1 A
6,440,385 B1 8/2002 Chaklader
(Continued)

FOREIGN PATENT DOCUMENTS

| CN | 102807483 | 12/2012 |
| JP | 61-167443 | 7/1986 |

(Continued)

OTHER PUBLICATIONS

International Search Report dated Apr. 28, 2015 in corresponding International (PCT) Application No. PCT/JP2015/052161.
(Continued)

*Primary Examiner* — Clinton A Brooks
(74) *Attorney, Agent, or Firm* — Wenderoth, Lind & Ponack, L.L.P.

(57) ABSTRACT

The present invention provides a novel hydrogenation reaction and hydrogenolysis reaction, and does not require a large scale hydrogen supply equipment and a high-pressure facility for a respective reaction. The present invention relates to a method for producing a hydrogenated compound, characterized in reducing a compound to be hydrogenated (C) using a hydrogen-containing compound (A) and a reduced compound (B) to produce the hydrogenated compound (c).

8 Claims, 2 Drawing Sheets

(51) Int. Cl.

| | | |
|---|---|---|
| C07C 29/132 | (2006.01) | |
| C07C 29/14 | (2006.01) | |
| C07C 29/143 | (2006.01) | |
| C07C 29/147 | (2006.01) | |
| C07C 29/20 | (2006.01) | |
| C07C 29/60 | (2006.01) | |
| C07C 45/41 | (2006.01) | |
| C07C 45/59 | (2006.01) | |
| C10G 45/22 | (2006.01) | |
| C10G 47/00 | (2006.01) | |
| C10G 65/12 | (2006.01) | |
| B01J 21/18 | (2006.01) | |
| B01J 23/44 | (2006.01) | |
| B01J 23/46 | (2006.01) | |
| B01J 23/652 | (2006.01) | |
| C07C 5/03 | (2006.01) | |
| C07C 29/141 | (2006.01) | |
| C07C 29/145 | (2006.01) | |
| C07C 29/149 | (2006.01) | |
| C07C 45/00 | (2006.01) | |

(52) U.S. Cl.
CPC ............ *B01J 23/6525* (2013.01); *C01B 3/08* (2013.01); *C07C 5/03* (2013.01); *C07C 29/132* (2013.01); *C07C 29/14* (2013.01); *C07C 29/141* (2013.01); *C07C 29/143* (2013.01); *C07C 29/145* (2013.01); *C07C 29/147* (2013.01); *C07C 29/149* (2013.01); *C07C 29/20* (2013.01); *C07C 29/60* (2013.01); *C07C 45/00* (2013.01); *C07C 45/41* (2013.01); *C07C 45/59* (2013.01); *C10G 45/22* (2013.01); *C10G 47/00* (2013.01); *C10G 65/12* (2013.01); *C07C 2521/18* (2013.01); *C07C 2523/44* (2013.01); *C07C 2601/14* (2017.05); *Y02E 60/36* (2013.01)

(56) References Cited

U.S. PATENT DOCUMENTS

| | | | |
|---|---|---|---|
| 6,600,078 | B1 | 7/2003 | Mahmud et al. |
| 7,632,483 | B2 * | 12/2009 | Marion .................... A62D 3/37 252/182.32 |
| 2002/0048548 | A1 | 4/2002 | Chaklader |
| 2002/0183513 | A1 * | 12/2002 | Grossmann ............. C07C 45/00 536/116 |
| 2004/0068149 | A1 | 4/2004 | Marion et al. |
| 2004/0092385 | A1 | 5/2004 | Timken |
| 2006/0116521 | A1 | 6/2006 | Fischer et al. |
| 2008/0272030 | A1 | 11/2008 | Boykin et al. |
| 2009/0005626 | A1 | 1/2009 | Hara et al. |
| 2009/0217922 | A1 | 9/2009 | Fukuoka et al. |
| 2011/0313212 | A1 * | 12/2011 | Kalnes .................. C07C 29/132 568/913 |
| 2012/0083631 | A1 | 4/2012 | Mirk et al. |
| 2013/0150623 | A1 | 6/2013 | Sajiki et al. |
| 2014/0363369 | A1 | 12/2014 | Sajiki et al. |

FOREIGN PATENT DOCUMENTS

| | | |
|---|---|---|
| JP | 3-202152 | 9/1991 |
| JP | 2003-512344 | 4/2003 |
| JP | 2004-505879 | 2/2004 |
| JP | 2004-196581 | 7/2004 |
| JP | 2004-525053 | 8/2004 |
| JP | 2005-272731 | 10/2005 |
| JP | 2005-537327 | 12/2005 |
| JP | 2006-347923 | 12/2006 |
| JP | 2007-31169 | 2/2007 |
| JP | 2007-45756 | 2/2007 |
| JP | 2008-285444 | 11/2008 |
| JP | 2009-275029 | 11/2009 |
| JP | 2010-84060 | 4/2010 |
| JP | 2010-137227 | 6/2010 |
| JP | 2011-148909 | 8/2011 |
| JP | 2012-17373 | 1/2012 |
| JP | 2012-527427 | 11/2012 |
| JP | 2013-10708 | 1/2013 |
| WO | 2007/100052 | 9/2007 |
| WO | 2010/016462 | 2/2010 |
| WO | 2012/023546 | 2/2012 |

OTHER PUBLICATIONS

Ruppert et al., "Hydrogenolysis Goes Bio: From Carbohydrates and Sugar Alcohols to Platform Chemicals", Angew. Chem. Int. Ed. Vo. 51, No. 11, 2012, pp. 2564-2601.

Extended European Search Report dated Jul. 11, 2017 in corresponding European Application No. 15744062.9.

Notice of Reasons for Refusal dated May 30, 2017 in corresponding Japanese Application No. 2015-559942, with English translation.

Roy, D. et al., "Aqueous phase hydrogenolysis of glycerol to 1, 2-propanediol without external hydrogen addition", Catalysis Today, vol. 156, No. 1-2, 2010, pp. 31-37.

Yuan, J. et al., "Copper-based catalysts for the efficient conversion of carbohydrate biomass into γ-valerolactone in the absence of externally added hydrogen", Energy & Environmental Science, vol. 6, 2013, pp. 3308-3313.

Jin, F. et al., "High-yield reduction of carbon dioxide into formic acid by zero-valent metal/metal oxide redox cycles", Energy & Environmental Science, vol. 4, No. 3, 2011, pp. 881-884.

Wang, L. et al., "Reduction of Nitroarenes to Aromatic Amines with Nanosized Activated Metallic Iron Powder in Water", Synthesis, 2003, No. 13, pp. 2001-2004.

Kruse, A. et al., "Hot compressed water as reaction medium and reactant, 2. Degradation reactions", The Journal of Supercritical Fluids, vol. 41, No. 3, 2007, pp. 361-379.

Hargus, C. et al., "Looped-oxide catalysis: a solar thermal approach to bio-oil deoxygenation", Energy & Environmental Science, vol. 7, 2014, pp. 3122-3134.

Xu, L. et al., "Highly efficient conversion of biomass-derived glycolide to ethylene glycol over CuO in water", Chem. Commun., vol. 50, 2014, pp. 6009-6012.

Notice of Reasons for Refusal dated Oct. 3, 2017 in corresponding Japanese Application No. 2015-559942, with English translation.

Communication Pursuant to Article 94(3) EPC dated May 8, 2018 in European Application No. 15744062.9.

* cited by examiner

[Figure 1]
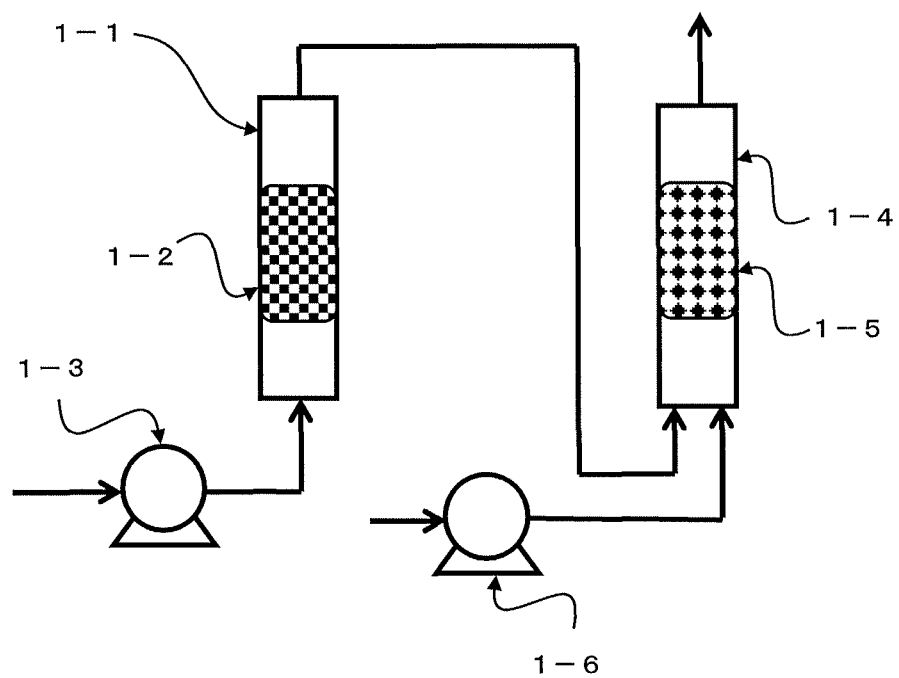

[Figure 2]
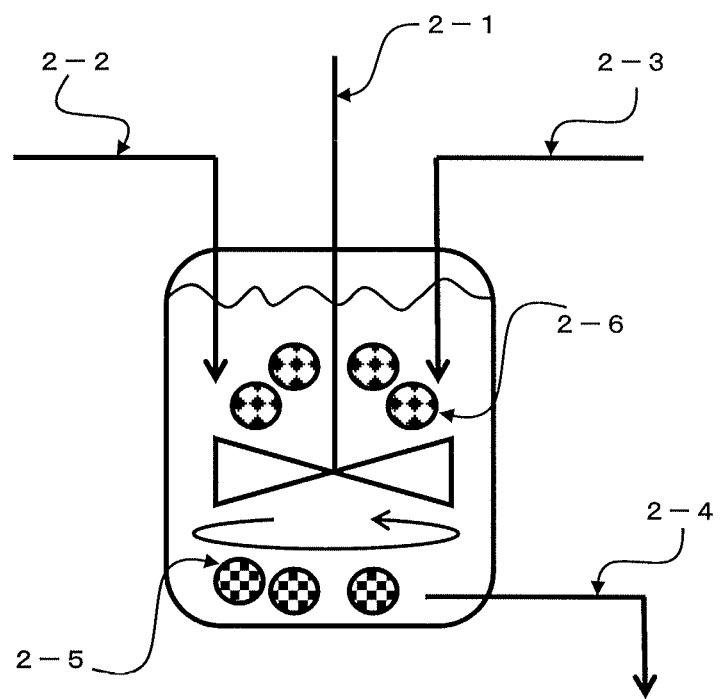

HYDROGENATION REACTION METHOD

TECHNICAL FIELD

The present invention relates to a method for hydrogenating a compound with hydrogen. Specifically, the present invention relates to a method for hydrogenating a compound to be hydrogenated using hydrogen obtained by reacting a hydrogen-containing compound and a reduced compound.

BACKGROUND ART

In the past, various methods for producing a saturated compound from an unsaturated hydrocarbon using hydrogen and for producing a new compound by hydrogenolysis of a hydrocarbon have been developed to be industrially utilized.

For example, Haber-Bosch process to obtain ammonia by reacting nitrogen and hydrogen in the presence of an iron catalyst under the condition of 20 atm and 500° C., a method for producing methanol from carbon monoxide and hydrogen at 50 to 100 atm in the presence of a catalyst such as copper oxide, a method for selectively hydrogenating a hydrocarbon such as acetylene and benzene, and a method for hydrocracking a hydrocarbon such as petroleum heavy oil and paraffin are exemplified. Recently, many technologies have been proposed, such as a method for hydrogenating a hydrocarbon by adding hydrogen in the presence of a catalyst such as molybdenum under high pressure (Patent Document 1), a method for synthesizing an olefin and the like from a normal paraffin and the like in the presence of a carrier obtained by supporting nickel, manganese and the like on a clay mineral under high pressure (Patent Document 2), a method for hydrocracking a hydrocarbon oil by using a catalyst which contains zeolite, silica-alumina and a metal (Patent Document 3), and a method for producing a higher hydrocarbon oil by hydrocracking a fat and oil (Patent Document 4).

In addition, recently, a technology for efficiently utilizing renewable sources with low environmental load has been necessary in terms of exhaustion of petroleum resources and climate change. A hydrogenation and a hydrogenolysis reaction of biomass resources have attracted attention as a technology for a renewable sources and future biorefinery. In particular, a carbon-carbon bond (C—C) and a carbon-oxygen bond (C—O) are cleaved by hydrogen in a hydrogenolysis reaction. A hydrogenolysis reaction can be effortlessly applied to the value chain of current chemical industry to be replaced, since a value-added core compound can be directly obtained by a hydrogenolysis reaction. In other words, the hydrogenation and a hydrogenolysis reaction of renewable sources may act as an intermediary between a currently available technology and a future biorefinery and have very high industrial value. For example, the intensive research for a hydrogenolysis of cellulose, glucose, glycerin, sugar alcohol or the like using a catalyst has been carried out (Non-patent Document 1).

Specifically, many methods have been proposed, such as a method for producing a hydrocarbon by preprocessing a biomass raw material such as cellulose in an alcohol and then carrying out a hydrogenolysis with a catalyst (Patent Document 5), a method for producing a sugar alcohol from cellulose under hydrogen-containing atmosphere and under pressure using a transition metal catalyst of 8 group to 11 group (Patent Document 6), a method for obtaining a reduced glycerin compound consisting of 1,2-propanediol, 1,3-propanediol, 1-propanol and 2-propanol with high selectivity by hydrogen reduction of glycerin in the presence of a catalyst (Patent Document 7), and a method for producing a hydrogenolysis compound such as butanediol by reacting 1,4-anhydroerythritol and hydrogen in the presence of a catalyst (Patent Document 8).

PRIOR ART DOCUMENT

Patent Document

Patent Document 1: JP 2011-148909 A
Patent Document 2: JP 2005-272731 A
Patent Document 3: JP 2010-137227 A
Patent Document 4: JP 2010-84060 A
Patent Document 5: JP 2012-17373 A
Patent Document 6: WO 2007/100052
Patent Document 7: JP 2009-275029 A
Patent Document 8: JP 2013-10708 A

Non-Patent Document

Non-patent Document 1: Angewandte Chemie-International Edition, 2012, vol. 51, no. 11, pp. 2564-2601

DISCLOSURE OF THE INVENTION

Problems to be Solved by the Invention

A conventional technology for hydrogenation and hydrogenolysis requires a high-pressure gas facility, since hydrogen is used as a raw material to react a target compound with hydrogen gas under pressure. As described in the above TECHNICAL FIELD, the reaction itself tends to be a high-pressure reaction and an excessive facility is needed. In addition, a conventional technology is disadvantageous in that a compound used as a reactant is restricted due to a high-pressure reaction.

Under the above-described circumstances, the objective of the present invention is to provide a method for easily and efficiently hydrogenating a compound without using a large scale hydrogen supply equipment and high-pressure facility.

Means for Solving the Problems

The inventors of the present invention made extensive studies to solve the above problems. As a result, the inventors achieved the present invention by finding that a compound can be hydrogenated and hydrocracked without dangerous hydrogen and a large scale equipment by using an activated hydrogen generated from a hydrogen-containing compound and a reduced compound.

Hereinafter, the present invention is described.

[1] A method for producing a hydrogenated compound, comprising
Step 1: the step of generating hydrogen by reacting a hydrogen-containing compound (A) and a reduced compound (B), and
Step 2: the step of producing the hydrogenated compound (c) by reducing a compound to be hydrogenated (C) with the generated hydrogen.

[2] The method according to the above [1], wherein the Step 1 and Step 2 are carried out in a one-pot way.

[3] The method according to the above [1] or [2], wherein the hydrogen-containing compound (A) is a protic compound.

[4] The method according to the above [1] or [2], wherein the hydrogen-containing compound (A) is at least one compound selected from the group consisting of a protic solvent, an organic acid and an inorganic acid.

[5] The method according to the above [1] or [2], wherein the hydrogen-containing compound (A) is a protic solvent.

[6] The method according to any one of the above [1] to [5], wherein the reduced compound (B) is at least one metal selected from the group consisting of Mg, Al, Si, Ti, V, Cr, Mn, Fe, Co, Ni, Cu, Zn, Ge, Zr, Nb, Mo, In, Sn, W and Ce.

[7] The method according to any one of the above [1] to [6], wherein the compound to be hydrogenated (C) is at least one compound selected from the group consisting of vegetable fat and oil, cellulose, sucrose, glucose, fructose, xylose, sorbitol, lactic acid, furfural, phenol and glycerin.

[8] The method according to any one of the above [1] to [7], wherein a hydrogenation catalyst (D) is further added in the Step 2.

Effect of the Invention

The present invention provides a novel hydrogenation reaction method. In the present invention, it is not necessary to use a large scale hydrogen supply equipment and a high-pressure facility for a respective reaction.

BRIEF DESCRIPTION OF THE DRAWINGS

FIG. 1 represents a continuous flow reactor as an embodiment of the present invention.

FIG. 2 represents a batch type reactor as an embodiment of the present invention.

MODE FOR CARRYING OUT THE INVENTION

The method for producing a hydrogenated compound according to the present invention is characterized in comprising Step 1: the step of generating hydrogen by reacting a hydrogen-containing compound (A) and a reduced compound (B), and Step 2: the step of producing the hydrogenated compound (c) by reducing a compound to be hydrogenated (C) with the generated hydrogen. Hereinafter, the compound and reaction condition for the present invention method are described in detail.

In the present invention, the term "hydrogenation" includes "hydrogenolysis" by which carbon-carbon bond and carbon-hetero atom bond are cleaved in association with the hydrogenation. In other words, the compound to be hydrogenated (C) includes a compound to be hydrocracked (C'), and the hydrogenated compound (c) includes a hydrocracked compound (c'). Hereinafter, if only the compound to be hydrogenated (C) or the hydrogenated compound (c) is described, the described compound respectively includes the compound to be hydrocracked (C') or the hydrocracked compound (c').

Step 1: Hydrogen Generating Stop
[Hydrogen-Containing Compound (A)]

In the present invention, the term "hydrogen-containing compound (A)" means a compound which has a hydrogen atom in the chemical structure thereof and which is not $H_2$. As the hydrogen-containing compound (A), any compound which is reduced by the reduced compound (B) and which generates hydrogen that contributes to the reaction may be used. For example, a protic compound may be used as the hydrogen-containing compound (A).

The term "protic compound" means a compound which has a proton donor group in the chemical structure. A proton donor group liberates a hydrogen atom as a proton and is exemplified by O—H and N—H. Such a protic compound is exemplified by a protic solvent, an organic acid and an inorganic acid.

The term "protic solvent" means a compound which has a proton donor group and which is liquid under ordinary temperature and ordinary pressure. In the present invention, for example, the term "ordinary temperature" is not lower than 20° C. and not higher than 30° C., and ordinary pressure is 1 atm. The protic solvent is exemplified by water; an alcohol solvent such as methanol, ethanol and isopropanol; a diol solvent such as ethylene glycol and propylene glycol; and an amine solvent such as propylamine and ethylenediamine.

The "organic acid" is exemplified by an organic carboxylic acid such as formic acid, citric acid, gluconic acid, succinic acid, acetic acid, oxalic acid, tartaric acid, lactic acid, fumaric acid, malonic acid, maleic acid and malic acid; a sulfonic acid such as methanesulfonic acid, trifluoromethanesulfonic acid, 10-camphorsulfonic acid, benzenesulfonic acid, p-toluenesulfonic acid and p-trifluoromethanesulfonic acid; and a sulfinic acid such as methanesulfinic acid, benzenesulfinic acid and p-chlorobenzenesulfinic acid. The "inorganic acid" is exemplified by hydrochloric acid, nitric acid, phosphoric acid, sulfuric acid, boric acid and hydrofluoric acid.

The hydrogen-containing compound (A) is preferably water, formic acid, acetic acid, malonic acid, citric acid, sulfonic acid and sulfinic acid, and more preferably water. Water is an ultimate renewable source and is easily reduced by the reduced compound (B) to generate hydrogen which contributes to the reaction. In addition, the reduced compound (B) becomes an oxidized compound (b), i.e. metal oxide, not being dissolved in water.

Only one hydrogen-containing compound (A) may be used, or two or more hydrogen-containing compound (A) may be mixed to be used. A solvent may be used in addition to the hydrogen-containing compound (A). The above-described protic solvent, organic acid and inorganic acid which are liquid under ordinary temperature and ordinary pressure, such as formic acid and acetic acid, may be also used as a solvent. In particular, water and an alcohol solvent such as methanol and ethanol may be used as a solvent. It is preferred that a solvent to be used other than the above-described protic solvent is not hydrogenated nor hydrocracked by the reaction of the present invention. Such a solvent is exemplified by an aliphatic hydrocarbon solvent such as hexane, octane, decane, tetradecane and hexadecane; an aromatic hydrocarbon solvent such as benzene, toluene, naphthalene and tetralin; and a cyclic hydrocarbon solvent such as cyclohexane and methylcyclohexane.

The hydrogen-containing compound (A) is reduced by the reduced compound (B) to generate hydrogen which contributes to the reaction. The term "hydrogen which contributes to the reaction" means activated hydrogen by which the compound to be hydrogenated (C) is hydrogenated or hydrocracked.

An amount of the hydrogen-containing compound (A) to be used may be decided depending on the requisite amount of the hydrogen which contributes to the reaction, and is not particularly restricted. The amount to the compound to be hydrogenated (C) is preferably not less than 1 time by mole and not more than 10 times by mole, and more preferably not less than 2 times by mole and not more than 5 times by mole. When the ratio is 1 time by mole or more, it may be ensured more certainly that the hydrogen of the amount which contributes to the reaction is sufficient to the compound to be hydrogenated (C). On the one hand, the ratio is excessively large, when the generated hydrogen may become excessive; therefore, the ratio is preferably 10 times by mole or less. However, when the hydrogen-containing compound (A) is used as a solvent, the amount of the hydrogen-containing compound (A) to be used may be largely excessive to the compound to be hydrogenated (C).

[Reduced Compound (B)]

In the present invention, the "reduced compound (B)" may be any compound which reduces the hydrogen-containing compound (A) in order to generate the hydrogen which contributes to the reaction, and should be stably ensured to be used for the reaction at any rate. For example, a metal or a metal oxide compound in a low oxidized state may be used as the reduced compound (B).

The element contained in the reduced compound (B) is not particularly restricted, and may be preferably at least one element selected from the group consisting of Mg, Al, Si, Ti, V, Cr, Mn, Fe, Co, Ni, Cu, Zn, Ge, Zr, Nb, Mo, In, Sn, W and Ce. Two or more elements may be mixed to be used. The element is more preferably at least one element selected from the group consisting of Fe, Mo, W and Ge, and is most preferably Fe. Fe is readily reduced to easily obtain the reduced compound and to easily generate the hydrogen which contributes to the reaction. In addition, since Fe has a valence of II or III and a redox reaction can be readily carried out using Fe, Fe can be recycled to be used. Furthermore, since Fe is abundantly present and inexpensive, Fe is easily available; therefore, when Fe is used, the hydrogenation reaction method of the present invention can be industrially carried out more economically.

The reduced compound (B) is oxidized to become the oxidized compound (b) by being reacted with the hydrogen-containing compound (A). On the one hand, the hydrogen-containing compound (A) generates the hydrogen which contributes to the reaction.

It is possible that the oxidized compound (b) is reduced to be the reduced compound (B) and to be reacted with the hydrogen-containing compound (A) again.

The reduced compound (B) may be either in a solid state or in a liquid state, and is preferably in a solid state. As a method for preparing the reduced compound (B), a physical mixing method, an impregnating method and a precipitation method can be used. A precipitation method is preferably used. The reduced compound (B) may be supported on a catalyst carrier which is used in a catalytic reaction. When the reduced compound (B) is a solid, the figure may be appropriately a pellet, a ball, a ring, a honeycomb or the like depending on the reaction.

An amount of the reduced compound (B) to be used is not particularly restricted and may be appropriately adjusted in the range in which hydrogen in an amount sufficient to hydrogenate the compound to be hydrogenated (C) can be obtained. For example, in the presence of the hydrogen-containing compound (A) in a sufficient amount, the amount of the reduced compound (B) may be adjusted to not less than 1 time by mole and not more than 20 times by mole to the compound to be hydrogenated (C).

[Reaction Condition]

The temperature for reacting the hydrogen-containing compound (A) and the reduced compound (B) may be not lower than 50° C. and not higher than 700° C., and preferably not lower than 100° C. and not higher than 500° C. The temperature of lower than 50° C. is not preferable, since a rate of hydrogen generation may possibly become insufficient. The temperature of higher than 700° C. is not preferable, since a redox rate may be possibly decreased by sintering the particle of the reduced compound (B) when the particle is used repeatedly.

The reaction may be carried out in both of gas-phase and liquid phase. When the reaction is carried out in gas-phase, an inert gas such as argon, helium and nitrogen may be used as a diluent gas. Even when the reaction is carried out in liquid-phase, the gas-phase part in a closed vessel may be substituted by the above-described inert gas.

The reaction pressure may be arbitrarily adjusted as long as the pressure is suitable for the reaction, and is preferably not lower than 0.01 MPa and not higher than 20 MPa. The reaction pressure of higher than 20 MPa is not preferable, since the economic efficiency may become lowered due to high cost of a reaction facility. The reaction pressure is more preferably not higher than 10 MPa or not higher than 5 MPa, and even more preferably not higher than 1.2 MPa, not higher than 0.8 MPa, not higher than 0.5 MPa or not higher than 0.2 MPa. The present invention can be worked with low reaction pressure by utilizing the hydrogen which is generated in the reaction system.

The reaction time is largely influenced by the reaction temperature, since the reaction time is dependent on the reaction rate. For example, when the reaction time is short, the reaction temperature may not sufficiently reach the predetermined temperature. As a result, the result becomes as if the reaction is carried out under lower temperature than the predetermined temperature. On the one hand, when the reaction time is long, not only excessive heat and time are not economical but also undesirable result may be yielded. It is exemplified as such an undesirable result that the reaction becomes very complicated due to a sequential reaction or a side reaction; as a result, a gasification rate is increased. The specific reaction time may be determined by confirming the consumption of the hydrogen-containing compound (A) and/or the reduced compound (B), preliminary experiment, or the like.

The oxidized compound (b) which is generated from the reduced compound (B) by the present invention reaction can be repeatedly used by reduction using a reducing agent. Such reducing agent is not particularly restricted, and any reducing agent can be used as long as the agent can reduce the oxidized compound (b). The reducing agent is preferably at least one selected from the group consisting of a dried gas of hydrogen, carbon monoxide, carbon hydride, and the like; a waste mainly composed of an organic substance; and biomass. The carbon hydride is exemplified by methane, and the waste is exemplified by a plastic waste. The temperature for the reduction of the oxidized compound (b) may be adjusted to not lower than 200° C. and not higher than 700° C., and preferably not lower than 300° C. and not higher than 500° C. When the temperature is lower than 300° C., the reduction rate of the oxidized compound (b) may not be sufficient. When the temperature is higher than 500° C., the oxidized compound (b) may be sintered; as a result, when such an oxidized compound (b) is repeatedly used, an oxidation-reduction rate may be decreased.

Step 2: Hydrogenation Step

In the hydrogenation reaction method according to the present invention, the hydrogen-containing compound (A) and the reduced compound (B) are reacted to generate hydrogen, and the compound to be hydrogenated (C) is converted to the hydrogenated compound (c) using the generated hydrogen.

The reaction of the hydrogen-containing compound (A) and the reduced compound (B) and the hydrogenation reaction of the compound to be hydrogenated (C) can be carried out in one reaction mixture.

[Compound to be Hydrogenated (C)]

The compound to be hydrogenated (C) is not particularly restricted as long as the compound is hydrogenated or hydrocracked by hydrogen. The compound is exemplified by carbon monoxide; carbon dioxide; an aromatic hydrocarbon compound such as benzene, phenol, styrene and naphthalene; a heteroaryl compound such as furan and furfural; a cyclic unsaturated hydrocarbon compound such as cyclohexene; a linear unsaturated hydrocarbon compound such as ethylene, acetylene and 1-decene; a nitro compound such as nitrobenzene; a nitrogen-containing compound such as an azo compound, a nitrile compound, an oxime compound and an amide compound; a ketone compound such as acetone, hydroxyacetone, dihydroxyacetone and cyclohexanone; an aldehyde compound such as crotonaldehyde; an oxoacid or a carboxylic acid, such as acetic acid and lactic acid; an alcohol compound such as pentanol; a synthetic hydrocarbon oil; a vegetable oil and fat, such as methyl laurate; a polysaccharide such as cellulose, cellobiose and sucrose; a monosaccharide such as glucose, fructose, xylose and erythritol; a sugar alcohol such as sorbitol and mannitol; a polyol such as glycerin; and the like. The compound to be hydrogenated (C) is preferably a vegetable oil and fat derived from a biomass; a saccharide such as cellulose and glucose; a sugar alcohol such as sorbitol; and a polyol such as glycerin. A plant-derived biomass is renewable carbon resources, since such a biomass absorbs carbon dioxide during a growing process thereof by photosynthesis. In addition, a plant-derived biomass may become chemical raw material which is stably supplied in terms of non-fossil resources. A plant-derived biomass therefore gives a large social impact and is important in view of an industrial perspective.

The compound to be hydrogenated (C) is hydrogenated or hydrocracked to be the hydrogenated compound (c) or the hydrocracked compound (c') by the hydrogen which is generated by the reaction of the hydrogen-containing compound (A) and the reduced compound (B). The hydrogenated compound (c) or hydrocracked compound (c') is exemplified by a higher alcohol obtained from a vegetable oil and fat; a hydrocarbon compound obtained from cellulose and glucose; 1,2-propanediol, 1,3-propanediol, 1-propanol and 2-propanol which are obtained from a sugar alcohol, propylene glycol, ethylene glycol or glycerin; butanediol obtained from 1,4-anhydroerythritol; and the like, but is not restricted thereto.

When a compound which has the function of the compound to be hydrogenated (C) is used as the hydrogen-containing compound (A) in order to be reacted with the reduced compound (B), a deoxidized compound can be obtained by simultaneously conducting both of the Step 1 and Step 2. Such an obtained deoxidized compound is similar to the hydrocracked compound (c'). In the present invention, the deoxidized compound is also referred to as the hydrocracked compound (c'). As the hydrogen-containing compound (A) which has the function of the compound to be hydrogenated (C), a synthetic hydrocarbon oil; a vegetable oil and fat, such as methyl laurate; a polysaccharide such as cellulose, cellobiose and sucrose; a monosaccharide such as glucose, fructose, xylose and erythritol; a sugar alcohol such as sorbitol and mannitol; a polyol such as glycerin; and the like are exemplified. The above-described deoxidized compound is exemplified by a higher alcohol such as $C_{6-20}$ alcohol; a hydrocarbon compound; a diol compound such as propylene glycol, ethylene glycol and butanediol; a $C_{1-4}$ alcohol such as propanol and ethanol; and the like.

The amount of the compound to be hydrogenated (C) to be used is not particularly restricted and appropriately adjusted. For example, the amount may be adjusted to an amount which is sufficiently hydrogenated or hydrocracked by the hydrogen which is generated in the above-described Step 1. Specifically, the amount may be adjusted to not less than 1 mol % and not more than 60 mol % to the reduced compound (B).

The concentration of the compound to be hydrogenated (C) as a raw material in the reaction mixture is not particularly restricted, and is preferably not less than 1 mass % and not more than 98 mass %, and more preferably not less than 10 mass % and not more than 60 mass %. When the concentration is less than 1 mass %, the production efficiency may be decreased and the present invention method may not possibly become suitable for commercial production. On the one hand, when the concentration is excessively high, the operability of the reaction mixture containing raw material compounds may possibly become poor and the reaction mixture may not possibly become suitable for commercial production due to higher viscosity. The reaction mixture may contain other components as long as the other components dos not inhibit the reaction of the present invention. As such other components, an antioxidant and a polymerization inhibitor are exemplified.

When the reaction is carried out in vapor phase, the concentration of the compound to be hydrogenated (C) as the raw material in the reaction gas is not particularly restricted. The concentration is preferably not less than 1 mass % and not more than 98 mass %, and more preferably not less than 5 mass % and not more than 40 mass %.

[Hydrogenation Catalyst (D)]

In the above-described hydrogenation reaction, a hydrogenation catalyst (D) may be used to further accelerate the hydrogenation reaction or hydrogenolysis reaction. As the hydrogenation catalyst (D) to be used, any metal element can be used as long as the metal element exhibits the catalytic function to hydrogenate or hydrocrack the compound to be hydrogenated (C). For example, the metal element selected from 6 group to 10 group in the periodic table is preferred, and it is preferred that the hydrogenation catalyst (D) contains at least one metal element selected from the group consisting of vanadium (V), chromium (Cr), manganese (Mn), iron (Fe), cobalt (Co), nickel (Ni), copper (Cu), zinc (Zn), molybdenum (Mo), ruthenium (Ru), rhodium (Rh), palladium (Pd), silver (Ag), tungsten (W), rhenium (Re), osmium (Os), iridium (Ir), platinum (Pt) and gold (Au). The metal element is more preferably cobalt (Co), nickel (Ni), copper (Cu), rhodium (Rh), palladium (Pd), iridium (Ir) or platinum (Pt). Not only the above-described metal element is a metal itself, but also an oxide and a sulfide thereof can be used. Two or more the hydrogenation catalysts (D) may be used in combination.

When the above-described metal element is used as the catalyst, the metal element may be supported on a solid carrier which has high specific surface area. As such a carrier, alumina; silica; titania; zirconia; an oxide of alkaline-earth metal, such as magnesia; an oxide of lanthanoid metal; a mixture thereof; a composite oxide; zeolite; clay mineral; activated carbon; or the like may be used.

The figure and configuration of the solid carrier are not particularly restricted, and exemplified by powder, particle, granule, pellet, honeycomb structure, extrusion figure, ring, cylinder, rib extrusion figure and rib ring. The size of the figure may be appropriately determined.

The amount of the supported metal element may be appropriately determined depending on various conditions such as the kind of the metal and the reaction, and may be adjusted to not less than 0.01 mass % and not more than 60 mass %, preferably not less than 0.01 mass % and not more than 30 mass %, and more preferably not less than 0.01 mass % and not more than 10 mass %. When the amount of the supported metal is lower than 0.01 mass %, the inversion rate of the raw material compound may be possibly decreased. On the one hand, when the amount of the supported metal is higher than 60 mass %, the economical efficiency may be possibly decreased due to high catalyst cost.

As a method for preparing the hydrogenation catalyst (D), a general preparation method can be applied. For example, the following methods are exemplified:

Impregnation method—a precursor of the catalytic component is dissolved in a solvent, and the catalytic component is supported on a carrier having high specific surface area using the solution;

Ion exchange method—a carrier having ion exchange capacity is added in a solution of a metal compound, and the metal is supported on the carrier by ionic bond;

Metal colloid method—a polymer or a surfactant is added in a solution of a metal salt, and reduction reaction is carried out to obtain homogeneous metal colloid.

An impregnation method is exemplified by equilibrium adsorption method, evaporation drying method and pore filling method. In an impregnation method and an ion exchange method, after the metal is supported on a carrier, washing, drying, firing and reduction are generally carried out. Then, the obtained catalyst is used in the reaction.

As the hydrogenation catalyst (D), micro particle noble metal black itself can be used. In order to activate the catalyst by reduction, the catalyst may be reduced using hydrogen under flow of an inert gas or a solvent which contains hydrogen gas.

The amount of the hydrogenation catalyst (D) to be used is not particularly restricted, and may be appropriately adjusted in the range in which the hydrogenation reaction or hydrogenolysis reaction is sufficiently accelerated. For example, the amount may be adjusted so that the hydrogenation reaction or hydrogenolysis reaction is sufficiently carried out by the hydrogen which is generated in the above-described Step 1. Specifically, the amount to the compound to be hydrogenated (C) may be adjusted to not less than 0.01 mass % and not more than 60 mass %, and more preferably not less than 0.1 mass % and not more than 20 mass %.

[Reaction Condition]

The temperature for hydrogenating or hydrocracking the compound to be hydrogenated (C) may be appropriately adjusted depending on the intended reaction, and is preferably not lower than 50° C. and not higher than 600° C. When the reaction temperature is excessively low, the conversion rate by the reaction may be decreased. On the one hand, when the temperature is excessively high, the quality of the product may be deteriorated due to by-product or the catalyst lifetime may be shortened. For the general reaction, the temperature is preferably not lower than 100° C. and not higher than 300° C., and more preferably not lower than 120° C. and not higher than 250° C. However, the temperature is not restricted to the above-described ranges.

The reaction pressure may be arbitrarily adjusted as long as the pressure is suitable for the reaction, and is preferably not lower than 0.01 MPa and not higher than 20 MPa. When the reaction pressure is higher than 20 MPa, the economic efficiency may become lowered due to high cost of a reaction facility. The reaction pressure is more preferably not higher than 10 MPa or not more than 5 MPa, and even more preferably not higher than 1.2 MPa, not higher than 0.8 MPa, not higher than 0.5 MPa or not higher than 0.2 MPa. The present invention can be worked under low reaction pressure by utilizing the hydrogen which is generated in the reaction system. For adjusting the pressure, an inert gas such as argon, helium and nitrogen can be optionally used.

The reaction time is largely influenced by the reaction temperature, since the reaction time is dependent on the reaction rate. For example, when the reaction time is short, the reaction temperature may not sufficiently reach the predetermined temperature and the result may become as if the reaction is carried out under lower temperature than the predetermined temperature. On the one hand, when the reaction time is long, not only excessive heat and time are not economical but also undesirable result may be yielded. It is exemplified as such an undesirable result that the reaction becomes complicated due to a sequential reaction or a side reaction; as a result, a gasification rate is increased or a large amount of hydrogen is consumed. The specific reaction time may be determined by confirming the consumption of the compound to be hydrogenated (C), preliminary experiment, or the like.

In the present invention, both of the above-described Step 1 and Step 2 may be carried out by one pot way. Specifically, at least the hydrogen-containing compound (A), the reduced compound (B) and the compound to be hydrogenated (C) are charged into a reaction vessel and the mixture is heated. As a result, the generation of hydrogen and the hydrogenation of the compound to be hydrogenated (C) can be carried out by one pot way. The reaction condition such as the reaction temperature and reaction time in such a case may be mainly adjusted similarly to the reaction condition of the above-described Step 2.

[Reaction Mode]

The mode of the hydrogenation reaction according to the present invention is not particularly restricted, and can be carried out in any mode such as batch mode, semi-batch mode and continuous flow mode. In the above-described hydrogenation reaction, the hydrogen-containing compound (A) and the compound to be hydrogenated (C) may be respectively in a state of gas or liquid. The whole reaction system in which the reduced compound (B) and the hydrogenation catalyst (D) are contained is not particularly restricted, and may be in any state of triphase of gas, liquid and solid, two-phase of gas and solid, and two-phase of liquid and solid. Hereinafter, each reaction mode is described.

(1) Continuous Flow Mode

When the hydrogenation reaction method of the present invention is conducted in continuous flow mode, the hydrogen-containing compound (A) is passed through the reactor in which the reduced compound (B) remains in order to generate hydrogen. Then, the hydrogenation reaction is conducted by passing the compound to be hydrogenated (C) with the generated hydrogen through the reactor in which the hydrogenation catalyst (D) remains (see FIG. 1). The hydrogenation catalyst (D) can be used as a fixed bed, a moving bed or a fluidized bed. A single reactor may be used, and successive multiple reactors may be also used.

From the reactor of the hydrogenation reaction, a reaction gas or a reaction solution which contains unreacted compound to be hydrogenated (C) and hydrogenated compound and/or hydrocracked compound is discharged. The hydrogenated compound and/or hydrocracked compound can be obtained by separation and purification from the reaction gas or reaction solution. The separation and purification method is not particularly restricted, and may be appropriately selected from ordinary methods such as distillation and extraction with considering the aspect or the like of the compound which is contained in the reaction mixture. The reduced compound (B) which remains in the reactor is converted to the oxidized compound (b). The oxidized compound (b) is recovered and reduced to be used as the reduced compound (B) in the next reaction. The above-described hydrogenation catalyst (D) is not necessarily activated for reuse, but may be timely activated for reuse by general activation method for solid catalyst supporting metal if needed.

In continuous flow mode liquid phase reaction as one embodiment of the present invention, liquid flow rate should be adjusted to the predetermined rate. Specifically, the liquid hourly space velocity is adjusted to not less than $0.1\ h^{-1}$ and not more than $10.0\ h^{-1}$ to produce hydrocarbon. The liquid hourly space velocity is preferably not less than $0.2\ h^{-1}$ and not more than $5.0\ h^{-1}$, and more preferably not less than $0.5\ h^{-1}$ and not more than $4.0\ h^{-1}$. When the liquid hourly space velocity is less than $0.1\ h^{-1}$, the amount of the raw material compound to be processed may be possibly small. When the liquid hourly space velocity is more than $10.0\ h^{-1}$, the reaction may not be possibly progressed sufficiently.

(2) Batch Reaction Mode

When the hydrogenation reaction method of the present invention is conducted in batch mode, at least the hydrogen-containing compound (A), the reduced compound (B) and the compound to be hydrogenated (C) are charged into a reactor to be reacted by heating and stirring (see FIG. 2). The hydrogenation catalyst (D) can be used as a fixed bed, a moving bed or a fluidized bed. A single reactor may be used, and successive multiple reactors may be also used.

After the reaction, the reaction mixture is subjected to solid-liquid separation. The liquid phase contains the hydrogenated compound and/or hydrocracked compound. The solid phase contains at least the hydrogenation catalyst (D) and the oxidized compound (b) which is generated by oxidizing the reduced compound due to the hydrogen-containing compound (A). A solid-liquid separation method is not particularly restricted, and may be appropriately selected from ordinary methods such as filtration method, centrifugation method and precipitation method with considering the figure and configuration of the catalyst, the amount of the unreacted raw material compound, or the like. The solid which contains the catalyst and unreacted raw material compound can be directly used in the next reaction. The above-described hydrogenation catalyst (D) is not necessarily activated for reuse, but may be timely activated for reuse by general activation method for solid catalyst supporting metal if needed.

Hereinafter, in addition to the above-described method for producing a hydrogenated compound according to the present invention, one example of a specific technology to which the present invention is applied is described.

The above-described technology relates to a method for processing biomass, and comprises the step of heating biomass in the presence of a reduced compound. Specifically, biomass is used as the compound to be hydrogenated (C) and as a raw material, and is degraded, deoxygenated and hydrogenated (i.e. reduced) by heating preferably at not lower than 100° C. and not higher than 600° C. in the presence of the reduced compound (B), preferably reduced iron, in order to obtain the hydrogenated compound (c) or the hydrocracked compound (c'). Hereinafter, the reaction of the technology is referred to as degradation, deoxygenization and hydrogenaration (i.e. reduction) reaction of biomass.

By the technology, the hydrocracked compound (c') can be directly obtained by the deoxygenization reaction between biomass and the reduced compound (B). In other words, even when the hydrogen-containing compound (A) is not used, the above-described degradation, deoxygenization and hydrogenaration (i.e. reduction) reaction is progressed. However, the hydrogen-containing compound (A) may be used.

The biomass which is subjected to the above degradation, deoxygenization and hydrogenaration (i.e. reduction) reaction may be any substance which is generally referred to as biomass. The biomass is exemplified by woody biomass such as unused wood, lumbering waste, driftwood and pruning waste; herbaceous biomass such as weed, grass, sugar cane and corn; excrementitious biomass such as food waste, garbage, sewage sludge and excrement (for example, poultry manure and cow dung). It is preferred to use inedible biomass, which cannot be used as food, among the above-described biomass.

The configuration of biomass is not particularly restricted. However, when biomass is in a solid state, it is preferred to preliminarily pulverize biomass in order to improve the reaction efficiency and handling performance. In particular, when the reaction is conducted using a fluidized bed, it is needed to use powdery biomass.

It is particularly preferred to use reduced iron as the reduced compound (B). Any reduced iron may be used as long as the reduced iron contains a reduced iron which is more hypoxic than triad iron and which has reduction ability. It is preferred that the reduced iron contains dyad, monad or zero-valent iron. The reduced iron is exemplified by $Fe_3O_4$, FeO and Fe. One reduced iron may be used and mixed reduced irons may be also used. For example, Fe(FeO) may be used.

The reduced iron is exemplified by FeO, $Fe_3O_4$, $Fe_2O_3$ and a mixture thereof, which are converted to the oxidized compound (b) by the reaction. The oxidized compound (b) is converted to the reduced compound (B) again by reduction to be reused in the above degradation, deoxygenization and hydrogenaration (i.e. reduction) reaction. The oxidized compound (b) can be reduced by bring the oxidized compound (b) into contact with a compound which has reduction action, such as hydrogen.

The hydrogenated compound (c) and hydrocracked compound (c') which are obtained by the reaction between biomass and the reduced compound contain relatively large amount of an aliphatic compound such as alkane and olefin.

When a solid acid such as zeolite, silica-alumina and heteropolyacid is further used in combination with the reduced compound (B), an aliphatic compound such as alkane and olefin can be converted and the obtained hydrogenated compound (c) and hydrocracked compound (c') contains many aromatic compounds. A noble metal such as Cu, Pt, Pd, Rh and Ru may be supported on the surface of the above-described solid acid such as zeolite. Such supporting may be carried out by ion exchange.

When the reduced compound (B) and a solid acid are used in combination for the degradation, deoxygenization and hydrogenaration (i.e. reduction) reaction of biomass in a batch type reactor, a flow type reactor or a fluidized bed type reactor, the reduced compound (B) and solid acid may be mixed to be used. When a flow type reactor or a fluidized bed type reactor is used, the reduced compound (B) is installed upstream for reduction and a solid acid is installed downstream to isomerize the obtained hydrogenated compound (c) and hydrocracked compound (c') to an aromatic compound.

Shale gas recently has attracted attention while it is believed that resources derived from petroleum will dry up in the future. The main component of shale gas is a lower alkane such as methane, and an amount of an aromatic compound produced from shale gas is small. It is worried that a circulation volume of an aromatic compound is decreased with the development of shale gas in the future. On the one hand, it is industrially significant that an aromatic compound is produced from biomass as a raw material.

During the above-described heating treatment, an inert gas may be used. By using such an inert gas, heating treatment can be homogeneously carried out, a heating treatment inhibitor which is generated during the heating treatment can be discharged to the outside of the system, and low-molecular-weight product can be transferred to the outside of the system. The gas is exemplified by nitrogen, carbon dioxide, helium, argon, an industrial exhaust gas and a mixed gas thereof, and is preferably inexpensive nitrogen, an industrial exhaust gas and a mixed gas thereof.

In addition to the above-described inert gas, a substance having reduction action, such as water vapor and hydrogen, may be added. An amount of the substance having reduction action to be used to the above-described inert gas is not less than 0 vol % and not more than 100 vol %, and preferably not less than 2 vol % and not more than 98 vol %. The substance having reduction action assists the reduction action of the reduced compound (B) and accelerates the degradation, deoxygenization and hydrogenaration (i.e. reduction) reaction of biomass, which is the hydrogen-containing compound (A) and the compound to be hydrogenated (C).

The temperature of the heating treatment is preferably not lower than 100° C. and not higher than 600° C., more preferably not lower than 150° C. and not higher than 550° C., and even more preferably not lower than 200° C. and not higher than 500° C.

As the reactor used for the above-described degradation, deoxygenization and hydrogenaration (i.e. reduction) reaction of biomass, a general reactor such as a batch type reactor, a flow type reactor, a fixed bed type reactor or a fluidized bed type reactor may be used, and a fluidized bed type reactor is preferred. Many woody biomass and herbaceous biomass, of which amount is very large, are solid, and reduced iron as particularly preferred reduced compound (B) is also solid. When a fluidized bed is used, the contact efficiency between the solid biomass and reduced iron can be maximized. In addition, it is preferred to install a device having heating function and heat removal function on the reactor, since initial heating is necessary for the above-described reaction and it may be sometimes needed to prevent overreaction during the reaction.

The generated hydrogenated compound or reduced compound (c) and the hydrocracked compound (c') can be separated and purified by an ordinary separation and purification means. Such a separation and purification means is exemplified by distillation, recrystallization, precipitation, membrane separation and column separation.

The method for producing the hydrogenated compound (c) and the hydrocracked compound (c') by degrading, deoxygenating and hydrogenating (i.e. reducing) biomass is specifically described as the following procedures. However, the present invention is not restricted to the following procedures as long as similar effect can be obtained by other procedures. For the sake of simplicity, the example in which reduced iron as the reduced compound (B) and zeolite supporting Pd as a solid acid supporting metal are used in combination in a flow type reactor is representatively described.

First, a reactor having an inert gas introducing port upstream and a discharge port downstream to discharge the hydrogenated (i.e. reduced) compound (c) and the hydrocracked compound (c') and an inert gas is used. Upstream of the reactor, powder of woody biomass and Fe(FeO) are installed. Downstream of the reactor, zeolite powder supporting Pd is installed. The zeolite powder is separated by a metal mesh.

Then, the reactor in the above device is heated by a heating means, and an inert gas and water vapor are introduced to the reactor in order to generate the hydrogenated (i.e. reduced) compound (c) and the hydrocracked compound (c') by heating biomass.

Further, the hydrogenated (i.e. reduced) compound (c) and the hydrocracked compound (c') obtained by the above-described heating treatment is converted to new compound by zeolite in the downstream. The new compound is discharged from the discharge port. By the above-described procedures, a method for producing a reduced compound obtained by degrading, deoxygenating and hydrogenating (i.e. reducing) biomass can be implemented.

According to the above-described present invention, a highly stable compound can be obtained by degrading, deoxygenating and hydrogenating (i.e. reducing) biomass.

The present application claims the benefit of the priority dates of Japanese patent application No. 2014-12925 filed on Jan. 28, 2014. All of the contents of the Japanese patent application No. 2014-12925 filed on Jan. 28, 2014, are incorporated by reference herein.

EXAMPLES

Hereinafter, the present invention is described in detail with Examples which are typical examples of the present invention and in which a batch type reactor was used. However, the present invention is not restricted to the following Examples as long as the effect of the present invention is exerted.

Example 1: Hydrogenation of Nitrobenzene

Iron powder was obtained by reducing iron oxide powder. Then, into a 50 mL stainless autoclave, nitrobenzene (0.4922 g, 4 mmol), iron powder (average particle diameter: about 60-80 nm, 0.6701 g, 12 mmol) and water (20 mL) were charged. The lid of the autoclave was closed. After the air in the autoclave was purged by nitrogen gas, the inside of the autoclave was heated at 120° C. using a heater with stirring the mixture by a magnetic stirrer. Then, after the mixture was stirred at 120° C. for 20 hours, heating was stopped and the autoclave was allowed to cool at room temperature. The reaction solution was taken from the autoclave which was cooled to room temperature, and the products in the solution were analyzed by gas chromatography. As a result, it was confirmed that nitrobenzene was hydrogenated to be aniline.

Examples 2 to 21

Into a 50 mL stainless autoclave, a compound to be hydrogenated described in Table 1, zinc powder having a particle diameter of 6 to 9 μm (0.395 g, 6 mmol, or 0.789 g, 12 mmol) or iron powder having a particle diameter of 60 to 80 nm (0.391 g, 6 mmol) as a reduced compound, water (20 mL) or a mixture of water (3 mL) and ethanol (17 mL) as a hydrogen-containing compound, and a hydrogenation catalyst described in Table 1 in some cases were charged. The lid of the autoclave was closed. The air in the autoclave was purged by nitrogen gas, and the internal pressure was adjusted to 0.5 MPa. The inside of the autoclave was heated at 180° C. using a heater with stirring the mixture by a magnetic stirrer, and the reaction was carried out for 20 hours. In only the case of Example 21, the internal temperature was adjusted to 165° C. and the reaction time was 5 hours. Then, heating was stopped and the autoclave was allowed to cool at room temperature. The reaction solution was taken from the autoclave. The solution was analyzed by high-performance liquid chromatography to identify the hydrogenated compound which was generated by hydrogenation of the compound to be hydrogenated and calculate the yield thereof. The results are shown in Table 1.

TABLE 1

| Example | (A) Hydrogen-containing compound | (B) Reduced compound | (C) Compound to be hydrogenated | (D) Hydrogenating catalyst | Yield of hydrogenated compound |
|---|---|---|---|---|---|
| 2 | water 3 mL ethanol 17 mL | zinc 0.789 g (12 mmol) | styrene 0.417 g (4 mmol) | — | ethylbenzene 58% |
| 3 | water 3 mL ethanol 17 mL | zinc 0.789 g (12 mmol) | 1-decene 0.561 g (4 mmol) | — | decane 73% |
| 4 | water 3 mL ethanol 17 mL | zinc 0.789 g (12 mmol) | cyclohexene 0.096 g (4 mmol) | activated carbon supporting 5% Pd 0.049 g | cyclohexane 31% |
| 5 | water 3 mL ethanol 17 mL | zinc 0.789 g (12 mmol) | cyclohexanone 0.393 g (4 mmol) | activated carbon supporting 5% Pd 0.049 g | cyclohexanol 90% |
| 6 | water 3 mL ethanol 17 mL | zinc 0.789 g (12 mmol) | benzaldehyde 0.425 g (4 mmol) | activated carbon supporting 5% Pd 0.049 g | benzyl alcohol 54% |
| 7 | water 20 mL | zinc 0.395 g (6 mmol) | cellulose 0.081 g (0.5 mmol) | activated carbon supporting 5% Ru 0.030 g | propylene glycol 8% |
| 8 | water 20 mL | zinc 0.395 g (6 mmol) | cellobiose 0.086 g (0.5 mmol) | activated carbon supporting 5% Ru 0.030 g | propylene glycol 18% mannitol 17% |
| 9 | water 20 mL | zinc 0.395 g (6 mmol) | sucrose 0.086 g (0.5 mmol) | activated carbon supporting 5% Ru 0.030 g | propylene glycol 34% |
| 10 | water 20 mL | zinc 0.395 g (6 mmol) | glucose 0.090 g (0.5 mmol) | activated carbon supporting 5% Ru 0.030 g | propylene glycol 34% |
| 11 | water 20 mL | zinc 0.395 g (6 mmol) | fructose 0.090 g (0.5 mmol) | activated carbon supporting 5% Ru 0.030 g | propylene glycol 32% |
| 12 | water 20 mL | zinc 0.395 g (6 mmol) | xylose 0.075 g (0.5 mmol) | activated carbon supporting 5% Ru 0.030 g | propylene glycol 27% |
| 13 | water 20 mL | zinc 0.395 g (6 mmol) | sorbitol 0.091 g (0.5 mmol) | activated carbon supporting 5% Ru 0.030 g | propylene glycol 11% mannitol 71% |
| 14 | water 20 mL | zinc 0.395 g (6 mmol) | mannitol 0.091 g (0.5 mmol) | activated carbon supporting 5% Ru 0.030 g | propylene glycol 25% |
| 15 | water 20 mL | zinc 0.789 g (12 mmol) | glycerin 0.368 g (4 mmol) | activated carbon supporting 5% Ru 0.030 g | propylene glycol 34% |
| 16 | water 20 mL | zinc 0.789 g (12 mmol) | lactic acid 0.090 g (1 mmol) | activated carbon supporting 5% Ru 0.030 g | propylene glycol 13% |
| 17 | water 20 mL | zinc 0.395 g (6 mmol) | dihydroxyacetone 0.181 g (2 mmol) | activated carbon supporting 5% Ru 0.030 g | propylene glycol 24% glycerin 14% |
| 18 | water 20 mL | zinc 0.395 g (6 mmol) | hydroxyacetone 0.165 g (2 mmol) | activated carbon supporting 5% Ru 0.030 g | propylene glycol 82% |
| 19 | water 20 mL | iron 0.391 g (6 mmol) | glucose 0.090 g (0.5 mmol) | activated carbon supporting 5% Ru 0.030 g | propylene glycol 16% |
| 20 | water 20 mL | iron 0.391 g (6 mmol) | sorbitol 0.091 g (0.5 mmol) | activated carbon supporting 5% Ru 0.030 g | propylene glycol 22% |
| 21 | water 20 mL | iron 0.391 g (6 mmol) | furfural 0.096 g (1 mmol) | activated carbon supporting 5% Ru 0.030 g | cyclopentanone 25% |

Example 22: Hydrogenation of Phenol

Into a 100 mL hastelloy autoclave, phenol (0.376 g, 4 mmol) as a compound to be hydrogenated, iron powder having a particle diameter of 60-80 nm (1.564 g, 24 mmol) as a reduced compound, water (40 mL) as a hydrogen-containing compound and 5% palladium catalyst supported on activated carbon (0.020 g) as a hydrogenation catalyst were charged. The lid of the autoclave was closed. After the air in the autoclave was purged by nitrogen gas, the internal pressure was adjusted to 1.0 MPa. The inside of the autoclave was heated at 230° C. using a heater with stirring the mixture by a mixing impeller. The reaction was conducted for 4 hours. Then, heating was stopped and the autoclave was allowed to cool at room temperature. The reaction solution was taken from the autoclave, and analyzed by gas chromatography to identify the hydrogenated compound which was generated by the hydrogenation of the compound to be hydrogenated and calculate the yield thereof. The result is shown in Table 2.

Example 23: Hydrogenation of Methyl Laurate

Into a 100 mL hastelloy autoclave, methyl laurate (0.870 g, 4 mmol) as a compound to be hydrogenated, iron powder having a particle diameter of 60-80 nm (1.564 g, 24 mmol) as a reduced compound, water (1 mL) as a hydrogen-containing compound, tetradecane mixture (40 mL) as a solvent and ruthenium-tin-molybdenum catalyst (0.0431 g) as a hydrogenation catalyst were charged. The lid of the autoclave was closed. The air in the autoclave was purged by nitrogen gas, and the internal pressure was adjusted to 0.1 MPa. The inside of the autoclave was heated at 270° C. using a heater with stirring the mixture by a mixing impeller, and the reaction was carried out for 24 hours. Then, heating was stopped and the autoclave was allowed to cool at room temperature. The reaction solution was taken from the autoclave. The solution was analyzed by gas chromatography to identify the hydrogenated compound which was generated by hydrogenation of the compound to be hydrogenated and calculate the yield thereof. The result is shown in Table 2.

TABLE 2

| Example | (A) Hydrogen-containing compound | (B) Reduced compound | (C) Compound to be hydrogenated | (D) Hydrogenating catalyst | Yield of hydrogenated compound |
|---|---|---|---|---|---|
| 22 | water 40 mL | iron 1.564 g (24 mmol) | phenol 0.376 g (4 mmol) | activated carbon supporting 5% Pd 0.020 g | cyclohexanone 34% cyclohexanol 10% |
| 23 | water 1 mL tetradecane 40 mL | iron 1.564 g (24 mmol) | methyl laurate 0.870 g (4 mmol) | Ru—Sn—Mo catalyst 0.0431 g | lauryl alcohol 61% |

INDUSTRIAL APPLICABILITY

The present invention relates to a novel hydrogenation reaction and can be applied to a general hydrogenation reaction. In addition, the present invention can be applied to the hydrogenation reaction which is carried out in the region apart from an industrial complex and in a small-scale space, since a conventional hydrogen storage facility and high pressure facility are not needed. The present invention is therefore superior in terms of applicability in comparison with conventional hydrogenation facilities.

EXPLANATION OF THE REFERENCE NUMERALS 1-1: Reactor for the hydrogen-containing compound (A) and the reduced compound (B)
1-2: Reduced compound (B)
1-3: Pump for introducing the hydrogen-containing compound (A)
1-4: Reactor for hydrogenation reaction of the compound to be hydrogenated (C)
1-5: Hydrogenation catalyst (D)
1-6: Pump for introducing the compound to be hydrogenated (C)
2-1: Agitator
2-2: Path for introducing the hydrogen-containing compound (A)
2-3: Path for introducing the compound to be hydrogenated (C)
2-4: Path for discharging the hydrogenated compound
2-5: Reduced compound (B)
2-6: Hydrogenation catalyst (D)

The invention claimed is:

1. A method for producing a hydrogenated compound, comprising
   step 1: generating hydrogen by reacting water (A) and a reduced compound (B) comprising Zn and/or Fe, and
   step 2: producing the hydrogenated compound (c) by reducing a compound to be hydrogenated (C) with the generated hydrogen at a temperature not lower than 120° C.,
   wherein step 1 and step 2 are carried out in a one-pot way, and
   the compound to be hydrogenated (C) is at least one selected from the group consisting essentially of biomass, vegetable fat and oil, cellulose, sucrose, glucose, fructose, xylose, sorbitol, lactic acid, furfural, phenol and glycerin.

2. The method according to claim 1, wherein a hydrogenation catalyst (D) is further added in the step 2.

3. The method according to claim 1, wherein the reduced compound (B) is Zn and/or Fe.

4. The method according to claim 1, wherein the compound to be hydrogenated (C) is at least one compound selected from the group consisting essentially of vegetable fat and oil, cellulose, sucrose, glucose, fructose, xylose and sorbitol.

5. The method according to claim 1, wherein the compound to be hydrogenated (C) is at least one compound selected from the group consisting essentially of cellulose and glucose.

6. The method according to claim 1, wherein the compound to be hydrogenated (C) is biomass.

7. The method according to claim 2, wherein the hydrogenation catalyst (D) is a metal, an oxide, or a sulfide comprising at least one metal element selected from the group consisting essentially of V, Cr, Mn, Fe, Co, Ni, Cu, Zn, Mo, Ru, Rh, Pd, Ag, W, Re, Os, Ir, Pt, and Au.

8. The method according to claim 2, wherein the hydrogenation catalyst (D) is a metal comprising at least one metal element selected from the group consisting essentially of Co, Ni, Cu, Rh, Pd, Ir, and Pt.

* * * * *